US007576136B2

(12) United States Patent
Parker et al.

(10) Patent No.: US 7,576,136 B2
(45) Date of Patent: Aug. 18, 2009

(54) EMULSIFIED FEEDSTOCK FOR HYDROCARBON PROCESS UNITS THAT INCORPORATE SPRAY ATOMIZATION

(75) Inventors: Wiley L. Parker, Conroe, TX (US); Alan E. Goliaszewski, The Woodlands, TX (US); Collin W. Cross, Houston, TX (US)

(73) Assignee: GE Betz, Inc., Trevose, PA (US)

( * ) Notice: Subject to any disclaimer, the term of this patent is extended or adjusted under 35 U.S.C. 154(b) by 539 days.

(21) Appl. No.: 11/146,954

(22) Filed: Jun. 7, 2005

(65) Prior Publication Data

US 2006/0276553 A1 Dec. 7, 2006

(51) Int. Cl.
*B01F 3/08* (2006.01)
*C10G 47/24* (2006.01)
*C07C 4/06* (2006.01)

(52) U.S. Cl. ......................... 516/21; 208/127; 208/130; 208/153; 208/157; 585/487; 585/652; 516/924

(58) Field of Classification Search .................. 516/21, 516/53, 924; 208/157, 153, 127, 130; 585/652, 585/487

See application file for complete search history.

(56) References Cited

U.S. PATENT DOCUMENTS

| | | | | |
|---|---|---|---|---|
| 2,698,284 | A * | 12/1954 | Adams | 208/85 |
| 3,781,226 | A * | 12/1973 | Schwartz | 502/62 |
| 5,283,001 | A * | 2/1994 | Gregoli et al. | 516/67 |
| 5,306,418 | A * | 4/1994 | Dou et al. | 208/157 |
| 6,368,367 | B1 * | 4/2002 | Langer et al. | 44/301 |
| 2004/0220284 | A1 * | 11/2004 | Parker et al. | 516/21 |

* cited by examiner

*Primary Examiner*—Daniel S Metzmaier
(74) *Attorney, Agent, or Firm*—Hoffman & Baron, LLP

(57) ABSTRACT

The present invention is directed to a method for producing an emulsified aqueous hydrocarbon solution comprising, providing a liquid hydrocarbon stream at a particular temperature and a separate water stream, mixing the water stream with a surfactant at a predetermined ratio, raising the pressure of the hydrocarbon stream to a pressure greater than the vapor pressure of steam at the temperature, spraying the water into the hydrocarbon stream at a pressure greater than that of the hydrocarbon stream in a pre-mix chamber; and passing the pressurized hydrocarbon-water mixture through a static mixing chamber.

7 Claims, 2 Drawing Sheets

EMULSIFIED FEEDSTOCK FOR HYDROCARBON PROCESS UNITS THAT INCORPORATE SPRAY ATOMIZATION

FIELD OF THE INVENTION

This invention relates to a spray atomization unit for use in an emulsified feedstock, particularly in a hydrocarbon process unit.

DESCRIPTION OF RELATED ART

Catalytic cracking is an important and widely used refinery process for converting heavy oils into gasoline and other lighter products. The catalytic cracking processes in use today can be classified as either moving bed or fluidized-bed units. The cracking process produces carbon which remains on the catalyst particle and rapidly lowers its activity. To maintain the catalyst activity at a useful level it is necessary to regenerate the catalyst by burning off the carbon with air. As a result, the catalyst is continuously moved from reactor to regenerator and back to the reactor. The cracking reaction is endothermic and the regeneration reaction is exothermic.

Average reactor temperature are in the range of 870 to 950 degrees Fahrenheit, with oil feed temperatures from 600 to 850 degrees Fahrenheit and regenerator exit temperatures for catalyst range from 1100 to 1250 degrees Fahrenheit.

The typical process flow for the catalytic cracking process includes: the hot oil feed is contacted with the catalyst in either the feed riser line or the reactor. As the cracking reaction progresses, the catalyst is progressively deactivated by the formation of coke on the surface of the catalyst. The catalyst and hydrocarbon vapors are separated mechanically and oil remaining on the catalyst is removed by steam stripping before the catalyst enters the regenerator. The oil vapors are taken overhear to a fractionation tower for separation into streams having the desired boiling ranges.

The spent catalyst flows into the regenerator and is reactivated by burning off the coke deposits with air. Regeneration temperatures are carefully controlled to prevent catalyst deactivation by overheating. This is generally done by controlling the airflow to give a desired CO2/CO ratio in the exit flue gases as the burning of CO to CO2 does not remove coke from the catalyst but only produces excess heat. Cyclone separators separate the flue gas and catalyst and the catalyst steam stripped to remove adsorbed oxygen before the catalyst is contacted with the oil feed.

The fluid catalytic cracking process employs a catalyst in the form of very fine particles, which behave as a fluid when aerated with a vapor. The fluidized catalyst is circulated continuously between the reaction zone and the regeneration zone and acts as a vehicle to transfer heat from the regenerator to the oil feed and reactor. The fresh feed and recycle streams are preheated by heat exchangers or a furnace and enter the unit at the vase of the feed riser where they are mixed with the hot regenerated catalyst. The heat from the catalyst vaporizes the feed and brings it up to the desired reaction temperature. The mixture of catalyst and hydrocarbons vapor travels up the riser into the reactors. The cracking reactions start when the feed contacts the hot catalyst in the riser and continues until the oil sent to the synthetic crude fractionators for separation into liquid and gaseous products.

Effective operation of several process units in hydrocarbon processing depends on the ability to atomize the hydrocarbon stream. In particular, for a fluid catalytic cracker, creation of small hydrocarbon droplets is a key contributor to unit efficiency as it promotes catalytic cracking over thermal cracking, which produces unwanted by products. Efficient atomization for these hydrocarbon processes has been the focus of numerous mechanical process changes. U.S. Pat. No. 5,306,418 for example discloses a nozzle, and fluidized catalytic cracking process using the nozzle for atomizing heavy feed to a riser reactor, are disclosed. A liquid feed stream is atomized by radial out-to-in impingement of atomizing vapor, discharged onto an impingement plug in an annular expansion region, then sprayed through an outlet. Baffles at the expansion region outlet, and an orifice outlet improve feed atomization and feed/FCC catalyst contact in a riser reactor. The nozzle may be used to distribute liquid over other reactor beds, or to add liquid to distillation columns.

The present invention provides an improved process for providing efficient catalytic cracking. The mechanical improvements according to the present invention include refinements such as inclusion of internal barriers to enhance turbulent flow within the FCC injection nozzle system, impingement blocks, and improved methods of spray blast. These approaches all rely on enhancing various factors known to be important in spray atomization. Another approach is to introduce an alternate mechanism of atomization. Generally, this is referred to as a secondary atomization. The basic premise is that primary atomization relies on the trade off between the cohesive nature of the fluid being sprayed and the aerodynamic forces impinging on a drop that drive breakup. Secondary atomization introduces a second factor that induces droplet breakup. This invention is a means of generating metastable water-in-oil emulsions. These emulsions are stabilized on the feed side of an atomizing system and then "explode" under spray conditions where the system pressure is released. The tiny droplets produced by this explosion provide benefits in the process environment. Key characteristics of this emulsion are the uniform distribution of small (5-10) micron water droplets in the oil at disperse phase concentrations that are large enough that the expansion work done by the exploding droplets is sufficient to overcome the cohesive energy of the hydrocarbon. The expanding gas explodes, demolishing a large droplet and producing smaller droplets. Secondary atomization as a means of improving combustions process is well established, for example U.S. Pat. No. 6,368,367, relates to an apparatus and process for making an aqueous hydrocarbon fuel composition, which includes: mixing a normally liquid hydrocarbon fuel and at least one chemical additive to form a hydrocarbon fuel-additive mixture; and mixing the hydrocarbon fuel-additive mixture with water under high shear mixing conditions in a high shear mixer to form the aqueous hydrocarbon fuel composition, the aqueous hydrocarbon fuel composition including a discontinuous aqueous phase, the discontinuous aqueous phase being comprised of aqueous droplets having a mean diameter of 1.0 micron or less.

However, there has been little if any application of this technology to the process field. For process units, the important criterion is that homogeneous water in oil emulsion of small droplet size we be formed and stabilized under process or modified process conditions. This is a significant departure from the application in a combustion environment where typically temperatures are lower.

It would therefore be desirable to have an apparatus and process for producing a meta-stable homogeneous oil water emulsion with small droplet sizes under the elevated temperature conditions typical of hydrocarbon process units, particularly fluid catalytic crackers.

SUMMARY OF THE INVENTION

The present invention is therefore directed to a method for producing an emulsified aqueous hydrocarbon solution comprising, providing a liquid hydrocarbon stream at a particular temperature and a separate water stream, mixing the water stream with a surfactant at a predetermined ratio, raising the pressure of the hydrocarbon stream to a pressure greater than the vapor pressure of steam at the temperature, spraying the water into the hydrocarbon stream at a pressure greater than that of the hydrocarbon stream in a pre-mix chamber; and passing the pressurized hydrocarbon-water mixture through a static mixing chamber.

According to the invention, there is provided a system and method for producing a meta-stable homogeneous oil water emulsion with small droplet sizes under the elevated temperature conditions typical of hydrocarbon process units, particularly fluidized catalytic crackers (FCC).

More particularly, this invention further provides for an apparatus for making an aqueous hydrocarbon composition, comprising: a surfactant additive storage tank, and a pump and conduit for transferring the surfactant to a water tank, a conduit for transferring a hydrocarbon process liquid from a process liquid source to an emulsion generator; a water conduit for transferring treated water from the water tank to an emulsion generator; a conduit for transferring an aqueous hydrocarbon process liquid composition from the emulsion generator to a process unit; a programmable logic controller for controlling: (i) the transfer of surfactant to a treated water tank; (ii) the transfer of hydrocarbon process liquid from the hydrocarbon source to the emulsion tank; (iii) the transfer of water from the treated water tank to the emulsion generator (iv) the mixing of the hydrocarbon process liquid and treated water in the emulsion generator; and (v) the transfer of the aqueous hydrocarbon process liquid from the emulsion tank to the process unit; and a computer for controlling said programmable logic controller.

DETAILED DESCRIPTION OF THE PREFERRED EMBODIMENT

Figure 1:
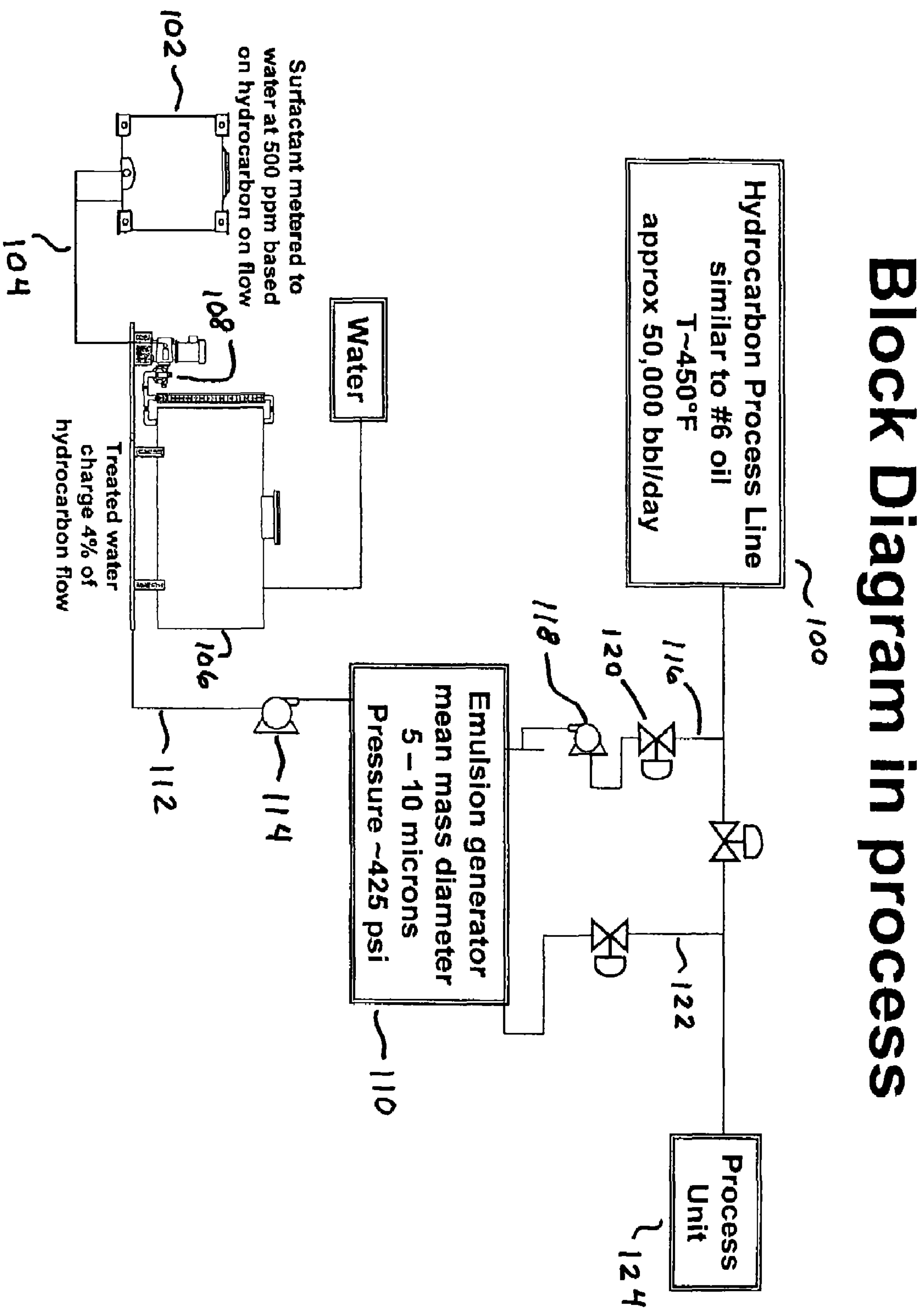
FIG. 1 is a block diagram of a hydrocarbon process unit according to the present invention.

There will be detailed below the preferred embodiments of the present invention with reference to the accompanying drawings. Like members are designated by like reference characters in all figures.

The present invention is directed to a system and method for producing a meta-stable homogeneous oil water emulsion with small droplet sizes under the elevated temperature conditions typical of hydrocarbon process units, particularly fluid catalytic crackers.

There are many aspects, which are important in the generation of metastable water in oil emulsion. Temperatures of the hydrocarbon feed immediately prior to the atomization nozzle are normally in excess of 350 degrees Fahrenheit; therefore, simple addition of water to such a stream would not generate an emulsion, but would instead produce steam. The secondary atomization process requires that the water entering the nozzle be in the liquid phase the expansion that occurs on steam formation is what drives the secondary atomization process.

The mechanical means used to generate the emulsified feedstock, the water in hydrocarbon, represent additions to the art. The feedstock should be homogeneously emulsified at the spray nozzle or the secondary atomization will be of lower overall efficiency. For the units in question the requirements that the aqueous component be present as a liquid temperature normally found in hydrocarbon process spray systems this pressure is significantly higher that that normally encountered. The emulsion plant must be capable of operating under these temperature and pressure conditions as well as being capable of handling the flows associate with the process unit. Experience with combustion systems indicates that drop size is a critical success factor for improved efficiency of atomization.

Turning now to FIG. 1, there is shown a block diagram of the process system according to the present invention. There is shown a hydrocarbon process input line 100, which supplies flow of hydrocarbon liquid to the process facility. For the purposes of this description, the hydrocarbon liquid is depicted in this example as being similar to #6 oil with a temperature of approximately 450 degrees Fahrenheit. An exemplary flow rate for such a process is provided for this description of approximately 50,000 barrels per day. There is also shown a tank containing a surfactant 102, with a feed pipe 104 to a treated water tank 106, with an inlet control valve 108, to control the input of surfactant from tank 102. The treated water tank 106 is also connected to a water input line 108. The surfactant in tank 102 is metered to the treated water tank at a predetermined rate to produce treated water with a known predetermined ratio of water and surfactant. The mixing rate is controlled by a programmable logic controller (not shown) which operates a valve such that the amount of surfactant provided into the water tank 106 can be controlled to the particular ratio required. The treated water tank 106 is connected to an emulsion generator 110 by a connector line 112. In the present example, a pump, 114 is also depicted as interposed between the treated water tank 106 and the emulsion generator, 110. The hydrocarbon process input line 100, is connected to the emulsion generator by hydrocarbon input line 116. The hydrocarbon input line 116, provides hydrocarbon liquid to the emulsion generator where it is mixed with the treated water from the treated water tank 106. The hydrocarbon input line 116, in this example there is also shown a pump 118 and valve 120 on the hydrocarbon input line. The pump and valve can be controlled by the programmable logic controller (not shown) in order to maintain the predetermined ratio of hydrocarbon liquid and treated water in the emulsion generator. There are many different types of emulsion generators available, but for this application it is imperative that the emulsion produced is uniform in both size of droplets introduced and in concentration of the two phases. An inline motionless mixer creates two layers of fluid for each element in the mixer. The practical importance of this is that the mixing increases exponentially with the number of elements, so for instance a 10 element static mixer produces $2^{10}$ or 1024 alternate fluid layers at the exit. The dimensions of the piping, flow rates and baffle elements then determine the effective droplet dimensions in the output fluid. This method also ensures very effective plug flow mixing and minimizes temperature, density and concentration gradients. The emulsified mixture, leaves the emulsion generator via the emulsion output line 122, where it is sent to the process unit 124. The emulsion leaving the emulsion generator, 110, is characterized in its physical properties as having a mean mass diameter s as having a mean mass diameter of 5 to 10 microns, at a pressure of approximately 425 pounds per square inch.

Figure 2:
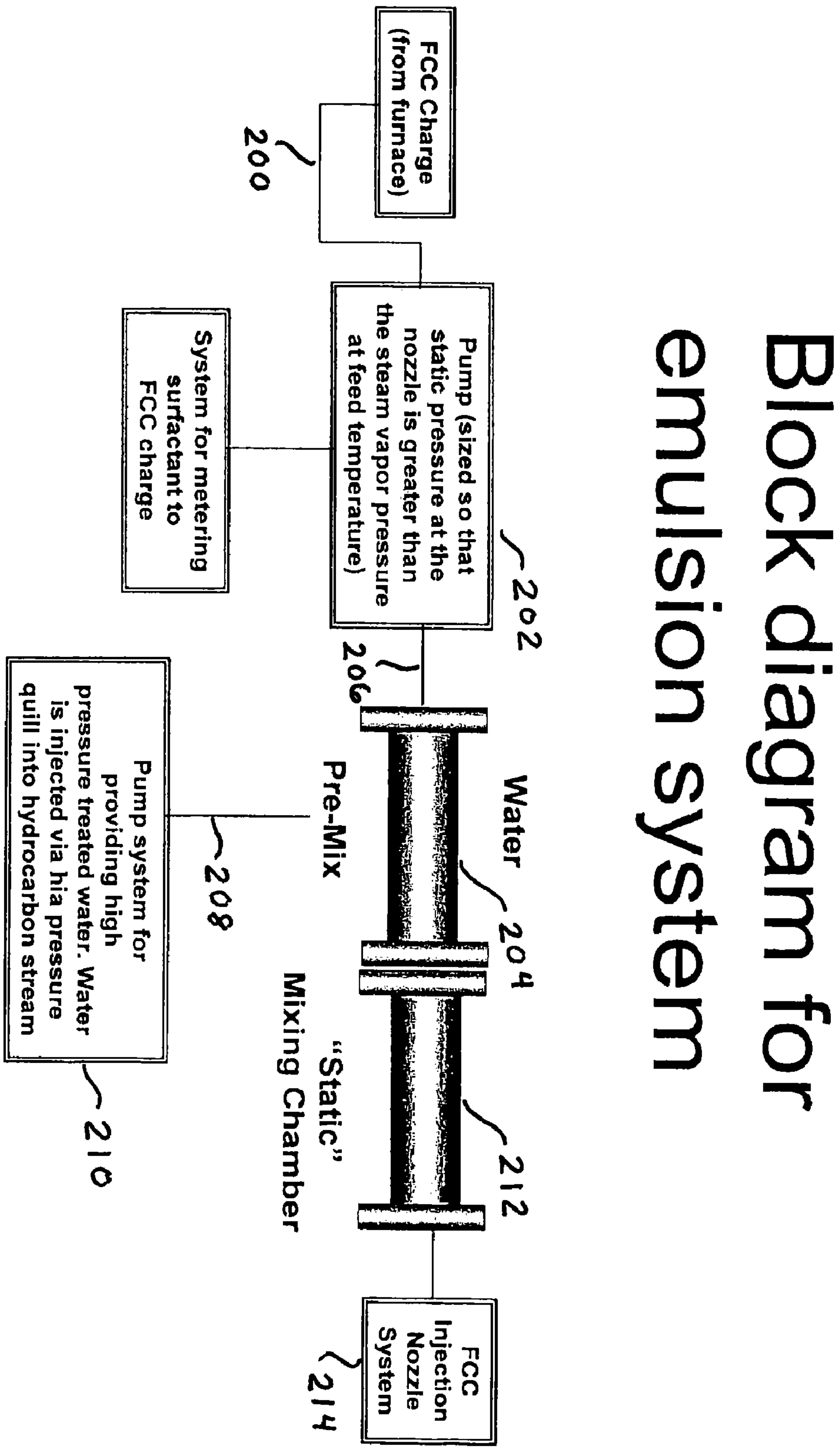
FIG. 2 is a block diagram of an emulsion system according to the present invention.

Turning now to FIG. 2, there is shown a block diagram of an emulsion system according to the present invention. Shown in FIG. 2 is an input line 200, delivering a Fluidized Catalytic Cracking charge from a furnace (not shown) through a pump 202. The pump 202 is controlled by a programmable logic controller (not shown) to regulate the flow rate of fluidized catalytic cracking charge from the furnace (not shown) into the pre-mix water chamber (204) via FCC hydrocarbon charge line 206. The pre-mix water chamber 204 receives the fluidized catalytic charge hydrocarbon stream and a treated water stream 208 from a pump 210. The pump 210 provides high pressure treated water from a treated water tank, (not shown in this view) via a high pressure quill into the hydrocarbon stream supplied via hydrocarbon feed line 206. The treated water pump 210 is also controlled by a programmable logic controller, to precisely regulate the flow of treated water into the pre-mix water chamber 204. The pre-mix water chamber 204 delivers the pre-mixed charge to the static mixing chamber 212 for the final emulsification step before the charge is delivered to the FCC injection nozzle system, 214.

The programmable logic controller (PLC), not shown in FIG. 1, is provided for controlling: (i) the transfer of surfactant from the additive storage tank 102 to the treated water storage tank; (ii) the transfer of treated water from the treated water tank 106 to the mixing chamber 204 of emulsion generator 110; (iii) the transfer of hydrocarbon process liquid from FCC charge inlet line 200 to the mixing chamber 204 of emulsion generator 110; (iv) the mixing in the emulsion generator 110 of the hydrocarbon process liquid and water additive mixture; and (vi) the transfer of the aqueous hydrocarbon process mixture from the emulsion generator 110 to process unit 124. The programmable logic controller stores component percentages input by the operator. The programmable logic controller then uses these percentages to define volumes of each component required. A blending sequence is programmed into the programmable logic controller, which electrically monitors all level switches, valve positions, and fluid meters.

In operation, the emulsification system consists of:

1) Raising the "back pressure" with pump 202 of the hydrocarbon feed exiting the final heat exchanger or furnace to a pressure greater than the vapor pressure of steam at that temperature.

2) As the fuel flows at a constant rate and pressure, water is sprayed into the hydrocarbon at a pressure greater than that of the hot hydrocarbon feedstock in pre-mix water chamber 204.

3) Passing the hot, pressurized hydrocarbon-water mixture through a static mixing chamber 212. The characteristics of this static mixing chamber are chosen so as to produce water droplets of appropriate mean mass diameter (5-10 micron). Static mixers work on the principles of diffusion, convection and shear to achieve homogeneous blends. Blending is thus a function of Reynolds Number, R, absolute viscosity, viscosity ratio of unmixed streams, density ratio of unmixed streams, volumetric ratio of unmixed streams, shear rate, element length to diameter ratio, and injection method. To this we add the further complication of working under hot pressurized streams where there is finite pumping capacity. We require that the final pressure after the mixing chamber maintain a working pressure greater than the steam vapor pressure at the working temperature. The pressure drop across the static mixer is given by:

4) $\Delta P=1.125\times10^{-3}$ fL $Q^2$ $\rho$/D)$C_{friction}$ where f=Darcy friction factor Q=flow Rate D=pipe inside diameter $\rho$=density (specific gravity)

$C_{friction}$=coefficient of friction caused by the static mixer element

The Reynolds number, $R_e$ describes the flow regime relevant to a fluid flowing through a pipe.

$R_e$=3157 Q $\rho$/($\mu$D)

Where Q=flow rate (gals/minute)

$\rho$=density (specific gravity)

$\mu$=viscosity (cps)

D=Pipe inside diameter (inch)

Rules of thumb indicate that to produce liquid-liquid dispersions of appropriate drop size, we require turbulent flow and minimum velocities through the static mixer of 5-10 ft/sec.

5) Use of high-pressure quills to pre-disperse the water in the hot, pressurized hydrocarbon feed in pre-mix water chamber 204. The feed is then fed to the static mixing chamber 212 to homogenize the water hydrocarbon mixture. This pre-dispersion of water reduces the severity of mixing required from the static mixers. This step reduces the pressure drop required for effective operation of the static mixers and thus the ultimate pumping capacity required in the feed system.

It will be appreciated that the present invention has been described herein with reference to certain preferred or exemplary embodiments. The preferred or exemplary embodiments described herein may be modified, changed, added to or deviated from without departing from the intent, spirit and scope of the present invention. It is intended that all such additions, modifications, amendments, and/or deviations be included within the scope of the claims appended hereto.

What is claimed is:

1. A method for producing an emulsified aqueous hydrocarbon in hydrocarbon processing comprising:

providing a liquid hydrocarbon stream at a particular temperature and a separate water stream;

mixing said water stream with a surfactant at a predetermined ratio;

raising the pressure of said hydrocarbon stream to a pressure such that water will remain a liquid at said temperature greater than the vapor pressure of steam at said temperature;

spraying said water into said hydrocarbon stream at a pressure greater than pressure of said hydrocarbon stream in a pre-mix chamber to define a pressurized hydrocarbon mixture;

passing said pressurized hydrocarbon mixture through a static mixing chamber having a plurality of mixing elements, producing a plurality of alternative fluid layers of liquid hydrocarbon and water in said chamber, and plug flow mixing the plurality of fluid layers to produce the emulsified aqueous hydrocarbon solution having water bubbles of appropriate mean mass diameter of 5 to 10 microns;

wherein the flow velocity of said pressurized hydrocarbon mixture through said static mixing chamber is in the range of 5-20 ft/sec.

2. The method for producing an emulsified aqueous hydrocarbon solution according to claim 1, wherein said predetermined ratio is 500 ppm of said surfactant to said pressurized hydrocarbon mixture.

3. The method for producing an emulsified aqueous hydrocarbon solution according to claim 1, wherein said premix chamber includes high pressure quills to pre-disperse the water stream.

4. The method for producing an emulsified aqueous hydrocarbon solution according to claim 1, wherein the hydrocarbon feedstock fluid properties are in the range of less than 0.95 specific gravity, and less than 14.5 cSt viscosity.

5. The method for producing an emulsified aqueous hydrocarbon solution according to claim 1, wherein the temperature is approximately greater than 212° F.

6. The method for producing an emulsified aqueous hydrocarbon solution according to claim 1, wherein said hydrocarbon stream has a residence time in the range of less than 30 sec.

7. The method for producing an emulsified aqueous hydrocarbon solution according to claim 1, wherein said water stream is in the range of 0.1-10% by mass of said hydrocarbon stream.

* * * * *

UNITED STATES PATENT AND TRADEMARK OFFICE

CERTIFICATE OF CORRECTION

PATENT NO. : 7,576,136 B2
APPLICATION NO. : 11/146954
DATED : August 18, 2009
INVENTOR(S) : Parker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this

Seventh Day of September, 2010

David J. Kappos

*Director of the United States Patent and Trademark Office*